United States Patent [19]

Kuhn et al.

[11] Patent Number: 5,385,846
[45] Date of Patent: Jan. 31, 1995

[54] BIOSENSOR AND METHOD FOR HEMATOCRIT DETERMINATION

[75] Inventors: Lance S. Kuhn; Mary L. Ochs, both of Fishers; Gilbert C. Morris, Anderson, all of Ind.

[73] Assignee: Boehringer Mannheim Corporation, Indianapolis, Ind.

[21] Appl. No.: 72,198

[22] Filed: Jun. 3, 1993

[51] Int. Cl.$^6$ ............................................. G01N 33/86
[52] U.S. Cl. .................... 436/70; 204/299 R; 204/403; 324/439; 422/82.01; 422/82.02; 422/82.03; 436/66; 436/150; 436/151
[58] Field of Search ............... 422/82.01, 82.02, 82.03; 436/66, 70, 150-151; 204/403, 299 R; 324/439

[56] References Cited

U.S. PATENT DOCUMENTS

| | | | |
|---|---|---|---|
| Re. 30,007 | 5/1979 | Steuer et al. | 324/30 |
| 3,922,598 | 11/1975 | Steuer et al. | 324/30 |
| 4,068,169 | 1/1978 | Angel et al. | 324/71 |
| 4,271,119 | 6/1981 | Columbus | 422/50 |
| 4,301,412 | 11/1981 | Hill et al. | 324/442 |
| 4,303,887 | 12/1981 | Hill et al. | 324/441 |
| 4,468,271 | 8/1984 | Pierson | 422/58 X |
| 4,547,735 | 10/1985 | Kiesewetter et al. | 324/450 |
| 4,686,479 | 8/1987 | Young et al. | 324/439 |
| 4,699,887 | 10/1987 | Abott et al. | 436/70 |
| 4,713,165 | 12/1987 | Conover et al. | 422/82.03 X |
| 4,734,184 | 3/1988 | Burleigh et al. | 204/409 |
| 4,835,477 | 5/1989 | Polaschegg et al. | 324/439 |
| 4,876,205 | 10/1989 | Green et al. | 436/66 |
| 4,963,814 | 10/1990 | Parks | 323/274 |
| 4,999,582 | 3/1991 | Parks et al. | 422/82.02 X |
| 4,999,632 | 3/1991 | Parks | 341/167 |
| 5,126,034 | 6/1992 | Carter et al. | 422/82.01 X |
| 5,243,516 | 9/1993 | White | 364/413.07 |

FOREIGN PATENT DOCUMENTS 0417796  3/1991  European Pat. Off. .
535485   4/1993  European Pat. Off. .

OTHER PUBLICATIONS

A. Caprani *Biochem. Bioenerg.* 1979, 6, 413–425.
Wampole Laboratories, STAT-CRIT Hematocrit/Hemoglobin Measuring Instrument Instruction Booklet, Oct. 1990.

Primary Examiner—James C. Housel
Assistant Examiner—Arlen Soderquist
Attorney, Agent, or Firm—D. Michael Young; Max J. Kenemore; Marilyn L. Amick

[57] ABSTRACT

A biosensor and method for determining the hematocrit level of a whole blood sample using electrochemistry. The biosensor includes working and counter electrodes. A porous membrane is impregnated with an electroactive compound and is spatially displaced from the surface of the electrodes. When a whole blood sample is applied to the porous substrate, a mixture of the electroactive compound and the blood is formed. The mixture settles on the electrodes and a potential difference is applied sufficient to oxidize or reduce the electroactive compound and generate a current. This current can be measured and correlated to hematocrit level.

18 Claims, 1 Drawing Sheet

BIOSENSOR AND METHOD FOR HEMATOCRIT DETERMINATION

BACKGROUND OF THE INVENTION

The invention relates to determining the hematocrit of a whole blood sample, specifically through the use of a biosensor and electrochemical techniques.

Hematocrit is the volume of red blood cells expressed as a percentage of the volume of whole blood in a blood sample. Hematocrit is used clinically to characterize blood. A low hematocrit indicates anemia (a low number of red blood cells and thus a reduced capacity for the blood to carry oxygen) and a high hematocrit may indicate polycythemia (a high number of red blood cells which may be a warning signal of serious circulatory failure). Hematocrit determination in the lab may provide an early diagnosis of these conditions.

U.S. Pat. No. 4,068,169 (Angel et al.), issued Jan. 10, 1978, discloses the measurement of hematocrit by passing a diluted volume of blood through sensing means, wherein conductivity changes in response to the presence of red blood cells passing through the sensing means.

U.S. Pat. No. 4,547,735 (Kiesewetter et al.), issued Oct. 15, 1985, discloses a hematocrit measuring device that includes upper and lower spatially displaced electrodes. A blood sample is added to the device and hematocrit level is correlated to changes in impedance of the blood sample.

U.S. Pat. No. 4,699,887 (Abbott et al.), issued Oct. 13, 1987, discloses a method of measuring the hematocrit level of blood by measuring the concentration of a marker (i.e. sodium ion) that has a different concentration in red blood cells versus plasma before and after lysing the red blood cells. The change in concentration of the marker after lysis can be correlated to the hematocrit level in the original blood sample.

U.S. Pat. No. 4,876,205 (Green et al.), issued Oct. 24, 1989, discloses an electrochemical assay for hemoglobin, wherein red blood cells are lysed and hemoglobin is assayed by monitoring the current changes produced on reduction of ferricyanide to ferrocyanide by hemoglobin.

U.S. Pat. No. 3,922,598 (Steuer et al.), issued Nov. 25, 1975, discloses an electrochemical apparatus for measuring hematocrit level of whole blood. The apparatus includes a pair of electrodes, a constant current source, and is calibrated so a plasma sample will give a reading of zero. When a probe is exposed to whole blood, the output voltage swings negatively. The magnitude or* this negative swing in voltage may be correlated to hematocrit level.

In addition, U.S. Pat. No. 4,835,477 (Metzner et al.), issued May 30, 1989, U.S. Pat. No. 4,686,479 (Baumeister et al.), issued Aug. 11. 1987, U.S. Pat. No. 4,303,887 (Hill et al.), issued Dec. 1, 1981, U.S. Pat. No. 4,301,412 (Hill et al.), issued Nov. 17, 1981, and U.S. RE 30007 (Enke et al.), issued May 22, 1979, all use conductivity measurements to determine the hematocrit level of a blood sample.

European Patent Application Publication No. 417796A (Ishihara), published Mar. 20, 1991, discloses an instrument which uses impedance to measure the hematocrit of a blood sample.

The STAT-CRIT ® device, a commercial hematocrit and hemoglobin measuring instrument, performs a hematocrit measurement based on blood resistivity, which increases as hematocrit increases.

SUMMARY OF THE INVENTION

This invention is based on the surprising result that adding an electroactive compound to a blood sample provides the basis for an electrochemical measurement of hematocrit.

The apparatus for measuring hematocrit, a disposable biosensor, has counter and working electrodes affixed to a first insulating substrate. A second insulating substrate overlays the electrodes and has a window exposing a portion of each electrode. A porous substrate impregnated with an electroactive compound is placed over the window, such that the substrate is spatially displaced from the electrodes.

The method of measuring hematocrit involves adding a sample of blood to the porous substrate. The blood sample dissolves the electroactive compound, thereby delivering the blood and compound mixture to the surface of the electrodes. A potential difference is then applied to the electrodes sufficient to oxidize or reduce the compound in the mixture and generate a current. Measurement of the current is the basis for the hematocrit measurement.

DETAILED DESCRIPTION OF THE INVENTION

The field of electrochemistry is based on the phenomenon that many metals, metal ions, and conjugated molecules easily accept and/or release electrons. The standard potential of an electroactive compound is the energy level at which the compound is equally inclined to release or accept electrons. Applying an electrical potential to an electrode which is more positive than the electrode's standard potential in a solution containing an electroactive compound causes oxidation (release of electrons) of the compound. Applying a potential to an electrode which is more negative than the electrode's standard potential in a solution containing an electroactive compound causes reduction (addition of electrons) of the compound. This invention relies on an electrochemical technique known as amperometry. Amperometry involves applying a potential and collecting the moving electrons as a current.

In the present invention, an electroactive compound is mixed with a blood sample. The amount of current generated by oxidation or reduction of the electroactive compound in this mixture may be correlated to the hematocrit level of the blood sample. The example which follows illustrates the preferred embodiment of the present invention.

Figure 1:
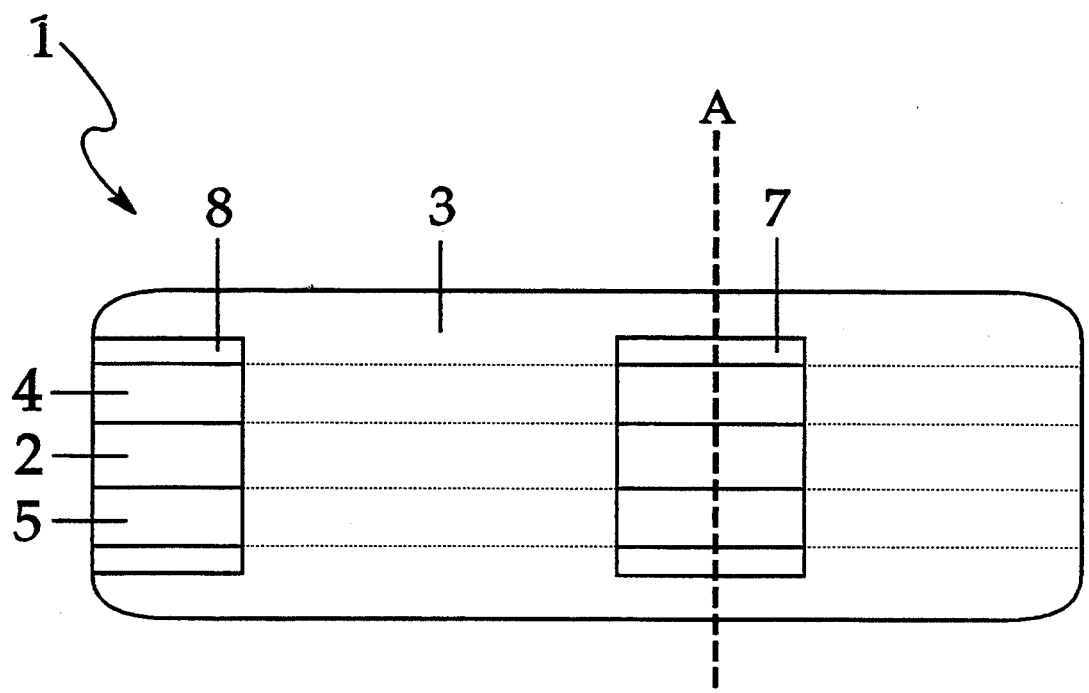
FIG. 1 is a schematic top view of a preferred embodiment of the biosensor, excluding the porous substrate and the cover mesh.
Figure 2:
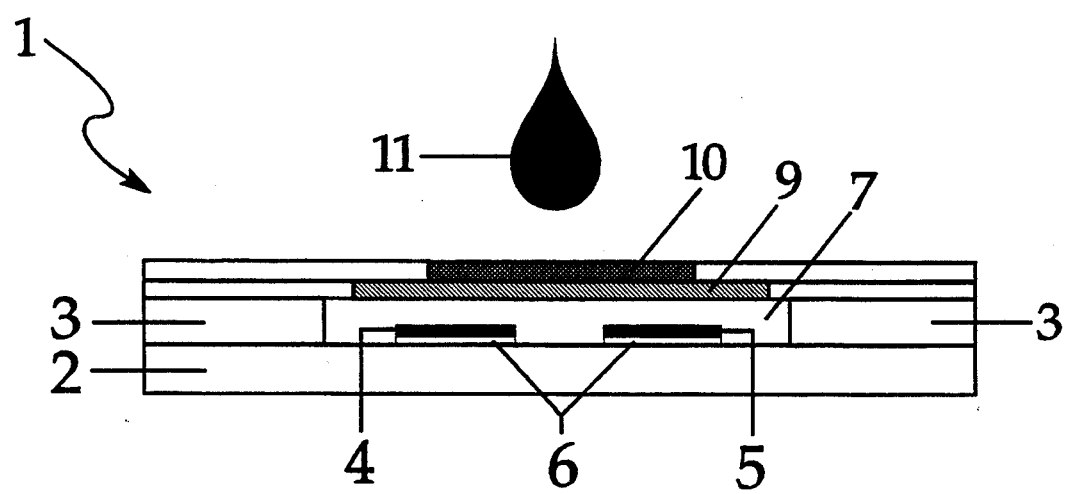
FIG. 2 is a schematic cross-sectional view of FIG. 1 taken along plane A of FIG. 1 and includes the porous substrate and cover mesh.

Reference is now made to FIGS. 1 and 2. Biosensor 1 has a first insulating substrate 2, which is about 360 microns thick and made of polyester. Working electrode 4 and counter electrode 5 are each about 0.1 micron thick, made of palladium, and are affixed to first insulating substrate 2 by the use of hot melt adhesive (not shown). Electrodes 4 and 5 are deposited on a backing of insulator material 6, a polyimide, to reduce the possibility of tearing the electrode before it is affixed to substrate 2. Backing 6 is about 25 microns thick. The electrode and polyimide combination is commercially available from Courtaulds Performance Films in California. Electrodes 4 and 5 extend from one end of substrate 2 to the other end in parallel configuration. The distance between electrodes 4 and 5 is about 1.2 millimeters (ram).

Substrate 3 is fixed on top of substrate 2 and electrodes 4 and 5 by the use of hot melt adhesive (not shown). Substrate 3 is about 250 microns thick, made of polyester, and includes window 7 which exposes substantially equal surface areas of electrodes 4 and 5. Window 7 is 4 mm by 6 mm and electrodes 4 and 5 are each 1.5 mm in width. Therefore, a surface area of about 6 $mm^2$ is exposed for each of the two electrodes. Substrate 3 also has cutout portion 8 at one end to allow an electrical connection between the electrodes and a power source (not shown) and a current measuring meter (not shown).

Biosensor 1 also has a polyester mesh 9. It is impregnated with a reagent that includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate butter), and a microcrystalline material (Avicel RC-591F - a blend of 88% microcrystalline cellulose and 12% sodium carboxymethylcellulose, available from FMC Corp.). Concentrations of the components within the reagent before drying are as follows: 400 millimolar (mM) ferricyanide, 55 mM ferrocyanide, 400 mM potassium phosphate, and 2.0% (weight:volume) Avicel.

Polyester mesh 9 is impregnated with the reagent describe above by dispensing six microliters (μL) of the reagent directly onto mesh 9. (Polyester mesh 9 may be impregnated with a surfactant or surface active agent in sufficient amount to aid in spreading the electroactive compound through the polyester mesh when manufacturing the biosensor.) Mesh 9 is then dried by heating at about 50° C. for about 15 minutes. The drying process removes at least about 90% of the water content of the reagent. After the reagent has dried, mesh 9 is affixed above window 7 on second insulating substrate 3 as shown in FIG. 2.

A polyester cover mesh 10 is then affixed to reagent-impregnated mesh 9 in order to protect mesh 9. Cover mesh 10 is impregnated with a surfactant in sufficient amount to aid in drawing blood sample 11 through cover mesh 10 and into reagent-impregnated mesh 9.

The reagent described above was made as follows:

Step 1: 7.45 grams (g) monobasic potassium phosphate and 60.14 g dibasic potassium phosphate were added to 400 g water Alter stirring, the resulting solution was adjusted to pH 8.0 with 6N potassium hydroxide.

Step 2: 20 g Avicel was added to 480 g water and stirred at high speed.

Step 3: the aqueous buffer from step 1 and the Avicel mixture from step 2 were combined in a beaker and stirred.

Step 4: 24.3 g ferrocyanide was slowly added to the mixture from step 3.

Step 5: 13 1.70 g ferricyanide was slowly added to the mixture from step 4, allowing the ferricyanide to dissolve as it was added.

Step 6: water was added to the mixture from step 5 until the beaker contained 1 liter of the mixture.

The biosensor apparatus described above may be used to determine the hematocrit level of a blood sample by the following method. Twenty microliter (μL) blood sample 11 is added to cover mesh 10, which delivers blood sample 11 to reagent-impregnated mesh 9, thereby forming a reagent and blood mixture which is deposited on the surface of electrodes 4 and 5. Twenty seconds after blood sample 11 is applied to biosensor 1, a potential difference or 500 millivolts is applied to the two electrodes. This twenty second time delay allows blood sample 11 sufficient time to hydrate the reagent and settle on electrodes 4 and 5.

When the potential difference is applied, the ferrocyanide at the surface of the more positively charged electrode is immediately oxidized to ferricyanide. Since oxidation is the process being measured in the embodiment described above, this electrode is called the working electrode by convention. The ferricyanide at the surface of the more negatively charged electrode is immediately reduced to ferrocyanide. This electrode is known as the counter electrode. Since the blood and reagent mixture is not stirred, additional ferrocyanide and ferricyanide in the blood and reagent mixture will diffuse to the surface of the working and counter electrodes respectively, where more ferrocyanide is oxidized to ferricyanide and more ferricyanide is reduced to ferrocyanide. The resulting current is known as a diffusion-limited current.

In the example above, the diffusional event which limits the amount of current generated is the diffusion of ferrocyanide to the surface of the working electrode. This diffusional event limits the current generated because current is proportional to the concentration of the electroactive compound at the surface of the electrode times the surface area of the electrode. In the example above, the surface areas of the working and counter electrodes are substantially equal, but the concentration of ferricyanide in the blood and reagent mixture is greater than the concentration of ferrocyanide in the blood and reagent mixture. As a result of this concentration difference, which occurs because more ferricyanide is added to the reagent than ferrocyanide, the current limiting event in the example described above is oxidation of ferrocyanide at the surface of the working electrode.

Measurement of this diffusion-limited current is the basis for a hematocrit measurement. When blood sample 11 is added to biosensor 1 as described above, a relationship is observed between hematocrit and current. As the hematocrit (percentage of red blood cells) of the blood sample increases, the current decreases.

The amount of ferrocyanide in the reagent mixture (before drying) discussed above must be present in sufficient amount to correlate current measurements to hematocrit level of the blood sample being measured. In the example discussed above, a concentration of 10 millimolar (mM) ferrocyanide was sufficient to correlate current measurements to hematocrit level in an assay. Below a 10 mM concentration of ferrocyanide, correlation of current to hematocrit level worsened until measurements of hematocrit level could no longer be made. Above a 10 mM concentration of ferrocyanide, correlation of current to hematocrit level improved until the reagent was saturated with ferrocyanide. Once the sample being measured was saturated with ferrocyanide, further increasing the amount of ferrocyanide worsened the correlation of current to hematocrit level due to the presence of undissolved ferrocyanide.

In the example discussed above, the amount of ferricyanide present in the reagent mixture must be in excess of the amount of ferrocyanide present. In order for the oxidation of ferrocyanide to be the current-limiting event, the amount of ferricyanide needs to be present in greater concentration than ferrocyanide. Precision of the biosensor was seen to improve as the concentration of ferricyanide increased until the sample being measured was saturated with ferricyanide. Increasing the amount of ferricyanide beyond the saturation point worsened precision and correlation of current to hematocrit level due to the presence of undissolved ferricyanide.

The upper limit of the amount of electroactive compound that may be incorporated into polyester mesh 9 will differ for different electroactive compounds due to the differences in solubility of those compounds in the reagent. The lower limit of the amount of electroactive compound that may be incorporated into polyester mesh 9 will also differ for different electroactive compounds due to differences in the amount necessary to correlate current measurements to hematocrit level of the blood sample being measured.

As an alternative to measuring the oxidation of ferrocyanide to ferricyanide in the example discussed above, the reduction of ferricyanide to ferrocyanide could be measured. In this case, the reduction of ferricyanide to ferrocyanide would be the current limiting step. The amount of ferricyanide in the reagent would be of critical importance, while the amount of ferrocyanide would only need to exceed the amount of ferricyanide.

The discussion above has described the preferred embodiment of the present invention. Variations of this invention are possible and will now be described.

Insulating substrates 2 and 3 may be of any useful thickness. The biosensor is intended to be mass produced from rolls of material, necessitating the selection of a material which is sufficiently flexible for roll processing and at the same time sufficiently rigid to give a useful rigidity to the finished biosensor. Typically, plastics, such as vinyl polymers and polyimides provide the electrical and structural properties which are desired.

In addition to palladium, other electrically conducting materials may be used for electrodes 4 and 5 including platinum, gold, silver, carbon, titanium, and copper. Noble metals are preferred because they provide a more constant, reproducible electrode surface area. Palladium is particularly preferred because it is one of the more difficult noble metals to oxidize. Silver is not preferred because it is more readily oxidized by air than the other metals listed above. Electrodes 4 and 5 must be sufficiently separated so that the electrochemical events at one electrode do not interfere with the electrochemical events at other electrode.

Polyester mesh 9 may be any porous substrate that has sufficient porosity to allow passage of a whole blood sample. Examples of substrates that may be used include meshes, films, soluble polymers, and membranes.

Examples of reversible electroactive compounds that could be used in place of ferricyanide are phenazine ethosulfate, phenazine methosulfate, phenylenediamine, 1-methoxy-phenazine methosulfate. 2,6-dimethyl-1,4-benzoquinone, 2,5-dichloro-1,4-benzoquinone, and 2,6-dichloro-1,4-benzoquinone.

In the alternative, a quasi-reversible electroactive compound or a non-reversible electroactive compound could be used. Depending on the standard potential of the compound chosen, a greater potential difference may have to be applied in order to cause oxidation or reduction of the compound. The standard potential of the electroactive compound (the energy level at which it is equally inclined to release or accept electrons) must be within the operating window of the electrode (the potential range where good electrochemical measurements can be made). The operating window for an electrode is defined on the positive end by the potential at which the electrode itself is oxidized and at the negative end by the reduction of oxygen and evolution of hydrogen from water.

The electrolyte present in the reagent described above may be a buffer or a salt, and is present to aid in the transfer of electrons at the electrode surface. The microcrystalline material is present in the reagent to aid in the dispersal of the reagent on the mesh during manufacturing. Examples of microcrystalline materials that may be used are microcrystalline cellulose, dextrans, and chitin. If the microcrystalline material is present below about 0.5% (weight:volume), the reagent is more likely to fall off of the mesh after drying. Above about 4.5% (weight:volume), the reagent gels.

As an alternative, porous substrate 9 could be eliminated and the reagent could be dispensed directly into window 7 of second insulating substrate 3. Cover mesh 10, if used would then be applied directly over window 7 of second insulating substrate 3.

This invention could also be practiced by impregnating porous substrate 9 with an electroactive compound alone, rather than the entire reagent described above.

The blood sample applied to the biosensor should be from about 10 microliters ($\mu L$) to about 50 microliters ($\mu L$). Sample volumes of less than about 10 microliters ($\mu L$) may not sufficiently hydrate the electroactive compound, resulting in a reduced current and poor precision. Sample volumes of greater than about 50 microliters ($\mu L$) may dilute the compound too much within the sample and result in a reduced current.

After the blood sample has been applied to the biosensor, application of the potential difference may be delayed from about 5 seconds to about 50 seconds. The potential difference applied between the electrodes should be sufficient to oxidize or reduce the electroactive compound but insufficient to oxidize or reduce other materials, like blood components or the electrode surface. The size of the potential difference is also related to the electrochemical properties of the electroactive compound. If the electroactive compound is reversible, adding only a small amount of energy to the standard potential will cause oxidation or reduction and therefore a smaller potential difference is required. Generally, if the electroactive compound is reversible, a potential difference of only about 120 millivolts is required. If the electroactive compound is not reversible, a much larger amount of energy may need to be added to the compound's standard potential in order to cause oxidation or reduction and therefore a larger potential difference will be required.

In the preferred embodiment described above, working electrode 4 and counter electrode 5 are substantially the same size and are made of the same electrically conducting material. However, other two electrode biosensors are possible. For example, the working and counter electrodes may be made of different materials and may be different sizes. Also, three electrode biosensors, including working, counter, and reference electrodes, are possible. In each case it is important that the current limiting event take place at the working electrode.

The meter described above will normally be adapted to apply an algorithm to the current measurement, whereby the hematocrit level is provided and visually displayed. Improvements in such a power source and meter are the subject of commonly assigned U.S. Pat. Number 4,963,814 (issued Oct. 16, 1990), U.S. Pat. No. 4,999,632, issued Mar. 12, 1991 (Application Ser. No. 07/451,212, filed Dec. 15, 1989), U.S. Pat. No. 4,999,582, issued Mar. 12, 1991 (Application Ser. No. 07/451,108, filed Dec. 15, 1989), and U.S. patent application Ser. No. 07/451,305 (filed Dec. 15, 1989; allowance granted by U.S. Patent Office Board of Pat. Appeals and Interferences on Sep. 24, 1992), the disclosures of which are hereby incorporated by reference.

What is claimed is:

1. An apparatus for measuring the hematocrit level of a blood sample, comprising:
   (a) a first insulating substrate;
   (b) working and counter electrodes affixed to the first insulating substrate;
   (c) a second insulating substrate, which overlays the working and counter electrodes, has a window for exposing a portion of the working and counter electrodes, and has a cut out portion at one end to allow contact between the electrodes and a meter and a power source; and
   (d) a porous substrate, which is impregnated with an electroactive compound, overlays the window, and is spatially displaced from the working and counter electrodes so that there is an empty space between the working and counter electrodes and the porous substrate prior to addition of the blood sample to the apparatus.

2. The apparatus of claim 1, wherein the electrically conducting material of the working and counter electrodes is palladium, platinum, gold, silver, titanium, copper, or carbon.

3. The apparatus of claim 2, wherein the working and counter electrodes are made of the same material and are substantially the same size.

4. The apparatus of claim 2, wherein the porous substrate is a mesh, a membrane, or a porous film.

5. The apparatus of claim 3, wherein the porous substrate is a polyester mesh.

6. The apparatus of claim 5, further comprising a cover mesh overlaying the porous substrate.

7. The apparatus of claim 5, further comprising:
   (e) a power source in electrical connection with the working and counter electrodes and capable of supplying an electrical potential difference between the working and counter electrodes sufficient to cause diffusion limited electrooxidation of a reduced form of the electroactive compound or diffusion limited electroreduction of an oxidized form of the electroactive compound at a surface of the working electrode; and
   (f) a meter in electrical connection with the working and counter electrodes and capable of measuring the diffusion limited current produced by the oxidation of the reduced form of the electroactive compound or the reduction of the oxidized form of the electroactive compound at the working electrode surface.

8. The apparatus of claim 7, wherein the cover mesh is impregnated with a surfactant or surface active agent in sufficient amount to aid in drawing the electroactive compound into the porous substrate when a blood sample is added to the cover mesh.

9. The apparatus of claim 8, wherein the porous substrate is impregnated with a reagent, the reagent comprising a reversible electroactive compound, an electrolyte, and a microcrystalline material.

10. The apparatus of claim 9, wherein the oxidized form of the electroactive compound is potassium hexacyanoferrate (III) and the reduced form of the electroactive compound is potassium hexacyanoferrate (II).

11. The apparatus of claim 10, wherein the porous substrate is also impregnated with a surfactant or surface active agent in sufficient amount to aid in spreading the electroactive compound throughout the porous substrate when manufacturing the biosensor.

12. A method of measuring the hematocrit level of a blood sample, comprising:
   (a) adding the blood sample to the porous substrate of the apparatus of claim 1, thereby forming a mixture of the electroactive compound and the blood sample, the mixture being deposited on a surface of the electrodes;
   (b) applying a potential difference between the working and counter electrodes that is sufficient to oxidize or reduce the electroactive compound in the mixture at the surface of the working electrode, thereby generating a current; and
   (c) measuring the current and correlating the current to hematocrit level.

13. The method of claim 12, wherein the electrically conducting material of the working and counter electrodes is palladium, platinum, gold, silver, titanium, copper, or carbon.

14. The method of claim 13, wherein the electrodes are made of the same material and are substantially the same size.

15. The method of claim 13, wherein the porous substrate is a polyester mesh.

16. A method of measuring the hematocrit level of a blood sample, comprising:
   (a) adding the blood sample to the porous substrate of the apparatus of claim 2, thereby forming an electroactive compound and blood sample mixture, which is deposited on a surface of the electrodes;
   (b) applying a potential difference between the electrodes that is sufficient to oxidize the electroactive compound in the mixture at the surface of one electrode and to reduce the electroactive compound in the mixture at the surface of the other electrode, thereby generating a current; and
   (c) measuring the current and correlating the current to hematocrit level.

17. The method of claim 16, wherein the porous substrate is a polyester mesh, a membrane, or a porous film.

18. The method of claim 17, wherein an oxidized form of the electroactive compound is potassium hexacyanoferrate (III) and a reduced form of the electroactive compound is potassium hexacyanoferrate (II).

* * * * *